(12) United States Patent
Kim et al.

(10) Patent No.: US 8,404,885 B2
(45) Date of Patent: Mar. 26, 2013

(54) HIGH ADHESIVE ACRYLATE MONOMER AND METHOD FOR PREPARING THE SAME

(75) Inventors: Woo-Sung Kim, Daejeon (KR); Jee-Seon Kim, Seoul (KR); Ja-Young Han, Daejeon (KR)

(73) Assignee: LG Chem, Ltd., Seoul (KR)

( * ) Notice: Subject to any disclaimer, the term of this patent is extended or adjusted under 35 U.S.C. 154(b) by 425 days.

(21) Appl. No.: 12/746,268

(22) PCT Filed: Dec. 3, 2008

(86) PCT No.: PCT/KR2008/007122
§ 371 (c)(1),
(2), (4) Date: Jun. 4, 2010

(87) PCT Pub. No.: WO2009/072798
PCT Pub. Date: Jun. 11, 2009

(65) Prior Publication Data
US 2010/0267982 A1    Oct. 21, 2010

(30) Foreign Application Priority Data
Dec. 6, 2007  (KR) .......................... 10-2007-0126265

(51) Int. Cl.
*C07C 261/00*    (2006.01)
*C07C 269/00*    (2006.01)
*C07C 271/00*    (2006.01)

(52) U.S. Cl. ....................................................... 560/27

(58) Field of Classification Search ..................... None
See application file for complete search history.

(56) References Cited

U.S. PATENT DOCUMENTS

| | | |
|---|---|---|
| 4,368,237 A | 1/1983 | Yamada et al. |
| 4,868,106 A | 9/1989 | Ito et al. |
| 5,574,134 A | 11/1996 | Waite |

OTHER PUBLICATIONS

Simo et al. (Electrophoresis, 2006, 27, 2250).*
Bruce P. Lee et al., "Synthesis of 3,4-dihydroxyphenylalanine (DOPA) containing monomers and their co-polymerization with PEG-diacrylate to form hydrogels", J. Biomaster. Sci. Polymer Edn, vol. 15. No. 4, pp. 449-464 (2004).
Bruce P. Lee et al., "Rapid Gel Formation and Adhesion in Photocurable and Biodegradable Block Copolymers with High DOPA Content", Macromolecules 2006, 39, pp. 1740-1748.
J. Org. Chem., vol. 41, No. 18, pp. 3056-3058, (1976).

* cited by examiner

*Primary Examiner* — Susanna Moore
*Assistant Examiner* — Jennifer C Sawyer
(74) *Attorney, Agent, or Firm* — McKenna Long & Aldridge LLP

(57) ABSTRACT

A high adhesive acrylate monomer has a specific chemistry figure. This monomer may be easily prepared in a simplified way, and various linkers may be used between L-DOPA and an acrylate group attached to a tail of L-DOPA, so molecular weight and size of the entire material may be easily controlled. Also, various kinds of acrylate to be combined to a isocyanate compound used as a linker may be selected, so various molecules may be easily composed.

6 Claims, No Drawings

HIGH ADHESIVE ACRYLATE MONOMER AND METHOD FOR PREPARING THE SAME

This application is a 35 U.S.C. §371 National Stage entry of International Application No. PCT/KR2008/007122, filed on Dec. 3, 2008, and claims priority to Korean Application No. 10-2007-0126265, filed on Dec. 6, 2007, which are all hereby incorporated by reference in their entireties.

TECHNICAL FIELD

The present invention relates to a high adhesive acrylate monomer and a method for preparing the same, and more particularly to a high adhesive acrylate monomer composed by introducing acrylate into a single molecule of 3,4-dihydroxyphenyl-L-alanine (L-DOPA) and a method for manufacturing the same.

BACKGROUND ART

In making displays or electronic devices, various kinds of materials are used. In some cases, adhesion is required between adjacent materials, so a suitable adhesive depending on the kind of adjacent materials is needed. However, adjacent materials are sometimes not easily adhered with each other using well-known adhesives, which makes a trouble in the adhesion work. Thus, there is a demand to develop an adhesive that ensures sufficient adhesive force regardless of kinds of adjacent materials.

3,4-dihydroxyphenyl-L-alanine (L-DOPA) is a single molecular material included in mussel adhesive protein (MAP) extracted from sea mussels and giving high adhesion. Commercial basic data for L-DOPA obtained through various property researches and applications may be found in papers, for example *J. Biomaster. Sci. Polymer Edn*, Vol. 15. No. 4, pp. 449-464 (2004); *Macromolecules*, 2006, 39, 1740-1748; and *JOC.*, Vol. 41, No. 18, pp. 3056, 1976, or US Publication No. 2003/0087338.

However, it would be understood that the compounds containing L-DOPA, disclosed in the above documents, are limited to copolymer derivatives useable in a glue form or monomers to which an amino group is coupled.

In order to overcome such biased technological development and also to give a sufficient cohesive or adhesive property as required, there is a demand to develop new high adhesive materials obtained from L-DOPA, and the present invention is designed under such backgrounds.

DISCLOSURE OF INVENTION

Technical Problem

The present invention is designed to solve the problems of the prior art, and therefore the present invention is directed to suggesting a new material obtained in a different way from L-DOPA conventionally used as an adhesive material, and a more convenient method for composing such a material, and also the present invention is directed to realizing a cohesive or adhesive property using the material regardless of substances to be adhered.

Technical Solution

In order to accomplish the above object, the present invention provides a high adhesive acrylate monomer, which has a following chemistry figure 1:

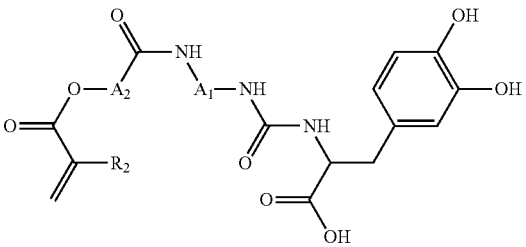

Chemistry FIG. 1 where R2 is hydrogen (—H) or a methyl group (—CH$_3$), and A1 and A2 are alkyl having 2 to 12 carbons (C2~C12), cycloalkyl having 3 to 8 carbons (C3~C8), aromatic cyclic compound having 6 to 12 carbons (C6~C12), or hetero compound, independently.

In another aspect of the present invention, there is also provided a method for preparing a high adhesive acrylate monomer, wherein a diisocyanate-based compound containing an acrylate group is combined with 3,4-dihydroxyphenyl-L-alanine (L-DOPA).

This method may be executed by (S1) methylating the 3,4-dihydroxyphenyl-L-alanine (L-DOPA); and (S2) adding the product of the step (S1) into the diisocynate-based compound containing an acrylate group.

At this time, the diisocyanate-based compound is preferably at least one of isophorone diisocyanate (IPDI), hexamethylene diisocyanate, methylene bis-(4-cychlohexylisocyanate), trimethyl hexamethylene diisocyanate, toluene-2,4-diisocyanate, and methylene diphenyl-4,4'-diisocyanate.

Meanwhile, the acrylate group contained in the diisocyanate-based compound is preferably at least one of hydroxy ethyl (meth)acrylate, hydroxy propyl (meth)acrylate, hydroxy butyl (meth)acrylate, hydroxy-poly(alkyleneoxy) alkyl (meth)acrylate, pentaerythritol hydroxy tri(meth)acrylate, dipentaerythritol hydroxy penta (meth)acrylate, and ditrimethylolpropane hydroxy trimethacrylate.

In the method for preparing a high adhesive acrylate monomer, the step (S1) preferably includes (S11) putting L-DOPA into methanol under a temperature condition of −50° C. to −20° C. and stirring the mixture; and (S12) slowly adding thionyl chloride whose amount is one to two times in comparison to mole of the L-DOPA, and then stirring the mixture for 12 to 24 hours to methylate the mixture.

BEST MODE FOR CARRYING OUT THE INVENTION

Hereinafter, preferred embodiments of the present invention will be described in detail. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

The following chemistry figure 2 shows a process of preparing a L-DOPA product, which is obtained from L-DOPA in the left side and methylated by reaction using thionyl chloride in a methanol solvent while increasing a temperature from −40° C. to a normal temperature.

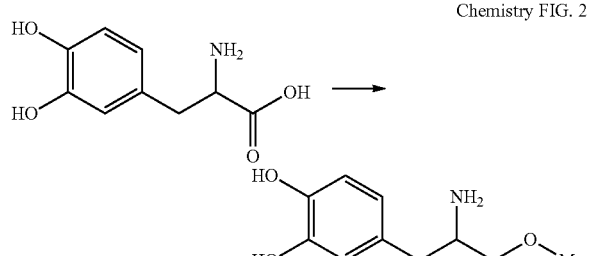

Chemistry FIG. 2

The following chemistry figure 3 shows a process of preparing a linker so as to introduce a diisocyanate-based compound containing an acrylate group to the methylated L-DOPA by component combination.

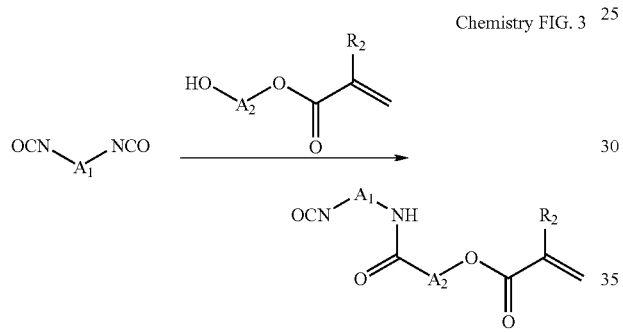

Chemistry FIG. 3

A1 and A2 expressed in the chemistry figure 3 are alkyl having 2 to 12 carbons (C2~C12), cycloalkyl having 3 to 8 carbons (C3~C8), aromatic cyclic compound having 6 to 12 carbons (C6~C12), or hetero compound, independently.

The diisocyanate-based compound shown as a product of the chemistry figure 3 may be isophorone diisocyanate (IPDI), hexamethylene diisocyanate (HDI), methylene bis-(4-cychlohexylisocyanate) (HMDI), trimethyl hexamethylene diisocyanate (TMHMDI), toluene-2,4-diisocyanate (TDI), and methylene diphenyl-4,4'-diisocyanate (MDI), or their mixtures.

The acrylate-based compound shown as a product of the chemistry figure 3 is a hydroxy alkyl acrylate-based compound, which preferably employs at least one of hydroxy ethyl (meth)acrylate, hydroxy propyl (meth)acrylate, hydroxy butyl (meth)acrylate, hydroxy-poly(alkyleneoxy) alkyl (meth)acrylate, pentaerythritol hydroxy tri(meth)acrylate, dipentaerythritol hydroxy penta (meth)acrylate, and ditrimethylolpropane hydroxy trimethacrylate.

If the methylated L-DOPA prepared according to the chemistry figure 2 is combined with the diisocyanate-based compound containing an acrylate group prepared according to the chemistry figure 3, a high adhesive acrylate monomer expressed in the chemistry figure 1 is prepared.

Now, the present invention is explained in more detail based on specific examples.

HEMA-IPDI that is one example of the product of the chemistry figure 3 was prepared according to the reaction expressed in the following chemistry figure 4. In detail, 97.81 g (440 mmol) of isophorone diisocyanate was put to 880 ml of n-hexane, and then 68.72 g (528 mmol) of hydroxy ethyl methacrylate (HEMA) was slowly added thereto over 20 hours at a normal temperature. After that, the solvent was removed by means of vacuum distillation, thereby obtaining HEMA-IPDI (P1) that is a reactive isocyanate as a product of the chemistry figure 4.

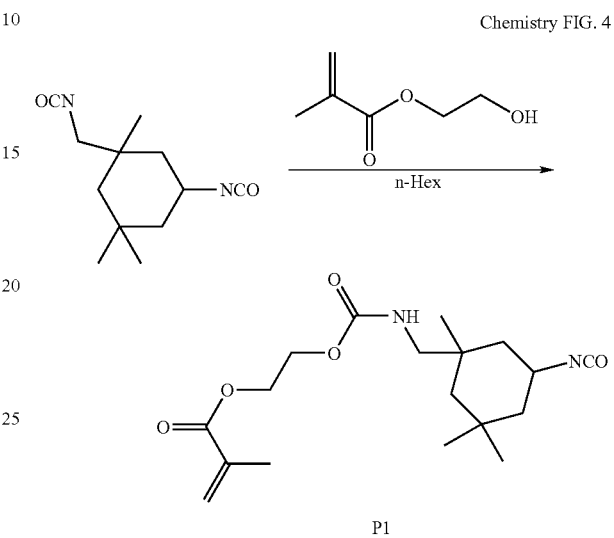

Chemistry FIG. 4

Meanwhile, the methylation of L-DOPA explained using the chemistry figure 2 was executed as follows. Namely, 3.94 g (20 mmol) of L-DOPA was put to 80 ml of methanol and then sufficiently stirred. After that, 1.6 ml (22 mmol) of thionyl chloride was slowly added thereto under a condition of −40° C. and then stirred for 18 hours, and then the solvent was vacuum-distilled. Acidity was set to pH 3 using sodium bicarbonate, and extraction was conducted using diethyl ether. Then, only organic solvents were collected and then vacuum-distilled again, thereby obtaining a product (P2) expressed in the following chemistry figure 5. NMR analysis data of the obtained product (P2) is as follows.

$^1$H NMR (500 MHz, CDCl$_3$) d 2.75 (dd, 1H), 3.05 (dd, 1H), 3.75 (m, 1H), 3.76 (s, 3H), 6.50 (m, 1H), 6.60 (m, 1H), 6.74 (m, 1H)

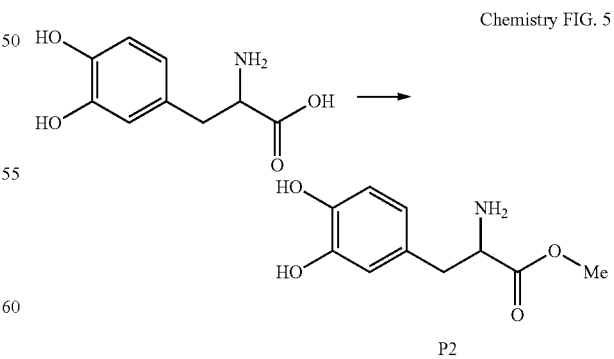

Chemistry FIG. 5

L-DOPA-acrylate was composed according to the following chemistry figure 6. In detail, 834.7 mg (2.37 mmol) of the product P1 expressed in the right side of the chemistry figure 4 was put into 13.2 g of cyclohexanone and then sufficiently stirred. Subsequently, 13 mg (0.02 mmol) of dibutyltin dilaurate and 500 mg (2.37 mmol) of the product P2 expressed in the right side of the chemistry figure 5 were added thereto and then reacted at 80° C. for 3 hours, thereby composing 10 wt % L-DOPA-acrylate in cyclohexanone (GC/MS M+563).

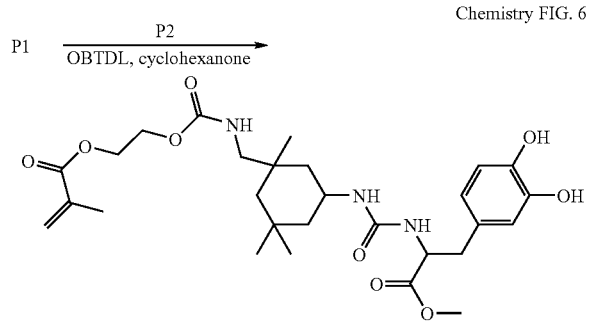

Chemistry FIG. 6

A hard coating solution using the high adhesive acrylate-based compound according to the present invention was set with compositions and contents as in the following table 1, which were classified into examples 1 to 3 and comparative examples 1 to 3. Then, the adhesive force test was conducted to each hard coating solution, and test results were compared.

Example 1

Components prepared according to materials and contents set in the following table 1 were added to a reactor, and then they were mixed until a coating solution would be uniform. At this time, L-DOPA acrylate was dissolved in cyclohexanone with the content of 10 weight % and then added to the reactor. After that, the coating solution was filtered using a filter with a size of 0.45 mm, thereby making a coating solution composition. The prepared coating solution composition was applied onto a COP film using a Meyer bar #12, and it was dried for about 4 minutes at 60 to 90° C. to form a film, and then UV was irradiated thereto with an intensity of 3,000 mJ/cm² to cure the coating solution composition, thereby forming a coating film.

Example 2

A coating film was formed in the same way as the example 1, except that a coating solution composition prepared as set in the following table 1 was applied onto a PET film using a Meyer bar #12.

Example 3

A coating film was formed in the same way as the example 1, except that a coating solution composition prepared as set in the following table 1 was applied onto a glass using a Meyer bar #12.

Comparative Example 1

A coating film was formed in the same way as the example 1, except that a coating solution composition prepared as set in the following table 1 was applied onto a COP film using a Meyer bar #12.

Comparative Example 2

A coating film was formed in the same way as the example 1, except that a coating solution composition prepared as set in the following table 1 was applied onto a PET film using a Meyer bar #12.

Comparative Example 3

A coating film was formed in the same way as the example 1, except that a coating solution composition prepared as set in the following table 1 was applied onto a glass using a Meyer bar #12.

TABLE 1

| Components | Examples | | | Comparative Examples | | |
|---|---|---|---|---|---|---|
| | 1 | 2 | 3 | 1 | 2 | 3 |
| Dipentaerythritol hexa acrylate | 9 | 9 | 9 | 9 | 9 | 9 |
| Pentaerythritol tetra acrylate | 1.6 | 1.6 | 1.6 | 1.6 | 1.6 | 1.6 |
| EB 600 | 16 | 16 | 16 | 16 | 16 | 16 |
| EB 294/25 HD | 0.2 | 0.2 | 0.2 | 0.2 | 0.2 | 0.2 |
| EB 9260 | 6 | 6 | 6 | 6 | 6 | 6 |
| L-DOPA acrylate | 10 | 10 | 10 | — | — | — |
| Daracur 1173 | 0.65 | 0.65 | 0.65 | 0.65 | 0.65 | 0.65 |
| Irgacure 184 | 0.65 | 0.65 | 0.65 | 0.65 | 0.65 | 0.65 |
| Irgacure 907 | 0.65 | 0.65 | 0.65 | 0.65 | 0.65 | 0.65 |
| Ethyl cellosolve | 25 | 25 | 25 | 25 | 25 | 25 |
| Ethanol | 8.33 | 8.33 | 8.33 | 8.33 | 8.33 | 8.33 |
| Ethyl acetate | 5 | 5 | 5 | 5 | 5 | 5 |
| n-butanol | 16.75 | 16.75 | 16.75 | 16.75 | 16.75 | 16.75 |
| Tego 270 | 0.1 | 0.1 | 0.1 | 0.1 | 0.1 | 0.1 |
| Tego 410 | 0.07 | 0.07 | 0.07 | 0.07 | 0.07 | 0.07 |

In the above table 1, EB 600, EB 294/25 HD, and EB 9260 are multi-acrylate product names of SK-UCB; Daracur 1173, Irgacure 184, and Irgacure 907 are initiator-related product names of Ciba; and Tego 270 and Tego 410 are dispersant product names of Degussa.

Adhesive Force Test

The cross cut Nichiban tape separation test was conducted to a crosslink-cured coating film formed on a substrate according to the examples 1 to 3 and the comparative examples 1 to 3, respectively. In detail, 11 scales reaching the substrate were marked on the coating film at an interval of 1 mm in length and width, respectively, to make 100 meshes of 1 mm². Then, a Nichiban tape was adhered thereto and then rapidly detached, which was repeated three times per each one. Then, the results were evaluated based on the following evaluation standard. The measurement results are shown in the following table 2.

<Evaluation Standards for the Adhesive Force Test>
good: crosslink-curing is possible after three repetitions
normal: the number of separated meshes after three repetitions is 1 to 50
bad: the number of separated meshes after three repetitions is 51 to 100

TABLE 2

| | Examples | | | Comparative Examples | | |
|---|---|---|---|---|---|---|
| | 1 | 2 | 3 | 1 | 2 | 3 |
| Evaluation Results | good | good | normal | bad | bad | bad |

As understood from the adhesive force evaluation results shown in the table 2, the examples of the present invention exhibit good results, at least normal. However, the comparative examples 1 to 3 exhibit bad test results. From the results, it would be clearly understood that the high adhesive acrylate-based compound according to the present invention gives a good adhesive force improving effect.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

INDUSTRIAL APPLICABILITY

The high adhesive acrylate monomer according to the present invention may be easily prepared in a simplified way, and various linkers may be used between L-DOPA and an acrylate group attached to a tail of L-DOPA, so molecular weight and size of the entire material may be easily controlled. Also, various kinds of acrylate to be combined to a isocyanate compound used as a linker may be selected, so various molecules may be easily composed.

The invention claimed is:

1. A high adhesive acrylate monomer, which has a following chemistry figure 1:

Chemistry FIG. 1

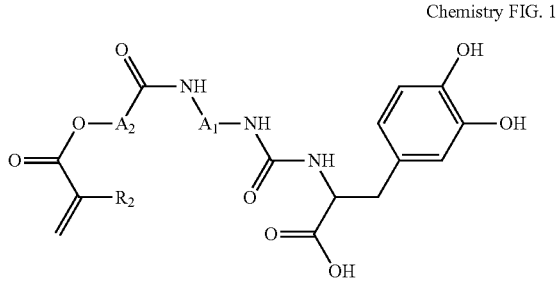

where $R_2$ is hydrogen (—H) or a methyl group (—$CH_3$), and $A_1$ and $A_2$ are alkanediyl having 2 to 12 carbons (C2-C12), cycloalkanediyl having 3 to 8 carbons (C3-C8), aromatic cyclic group having 6 to 12 carbons (C6~C12), or heteroalkanediyl, independently.

2. A method for preparing a high adhesive acrylate monomer,
wherein a diisocyanate-based compound containing an acrylate group is combined with methylated 3,4-dihydroxyphenyl-L-alanine (L-DOPA) to prepare a high adhesive acrylate monomer defined in claim 1.

3. The method for preparing a high adhesive acrylate monomer according to claim 2, wherein the method is executed by:
(S1) methylating the 3,4-dihydroxyphenyl-L-alanine (L-DOPA); and
(S2) adding the product of the step (S1) into the diisocynate-based compound containing an acrylate group.

4. The method for preparing a high adhesive acrylate monomer according to claim 2,
wherein the diisocyanate-based compound is at least one material selected from the group consisting of isophorone diisocyanate (IPDI), hexamethylene diisocyanate, methylene bis-(4-cychlohexylisocyanate), trimethyl hexamethylene diisocyanate, toluene-2,4-diisocyanate, and methylene diphenyl-4,4'-diisocyanate.

5. The method for preparing a high adhesive acrylate monomer according to claim 2,
wherein the acrylate group contained in the diisocyanate-based compound is at least one selected from the group consisting of hydroxy ethyl (meth)acrylate, hydroxy propyl (meth)acrylate, hydroxy butyl (meth)acrylate, hydroxy-poly(alkyleneoxy)alkyl (meth)acrylate, pentaerythritol hydroxy tri(meth)acrylate, dipentaerythritol hydroxy penta (meth)acrylate, and ditrimethylolpropane hydroxy trimethacrylate.

6. The method for preparing a high adhesive acrylate monomer according to claim 3, wherein the step (S1) includes:
(S11) putting L-DOPA into methanol under a temperature condition of −50° C. to −20° C. and stirring the mixture; and
(S12) slowly adding thionyl chloride whose amount is one to two times in comparison to mole of the L-DOPA, and then stirring the mixture for 12 to 24 hours to methylate the mixture.

* * * * *